United States Patent [19]

Birks et al.

[11] Patent Number: 4,656,141
[45] Date of Patent: Apr. 7, 1987

[54] HIGH-PERFORMANCE LIQUID CHROMATOGRAPHY PROCESS AND APPARATUS AND COMPOSITION OF MATTER THEREFOR

[75] Inventors: John W. Birks, Boulder, Colo.; Mitchell S. Gandelman, Newington, Conn.

[73] Assignee: University Patents, Inc., Westport, Conn.

[21] Appl. No.: 536,096

[22] Filed: Sep. 27, 1983

[51] Int. Cl.[4] .................... G01N 21/75; G01N 30/02; G01N 33/00

[52] U.S. Cl. .................................... 436/172; 436/94; 436/128; 436/131; 436/132; 436/140; 436/161; 436/111

[58] Field of Search ................. 436/172, 94, 905, 128, 436/131, 132, 140, 161

[56] References Cited

PUBLICATIONS

Birks et al., "Photochemical Reaction Detection in HPLC", *Trends in Anal. Chem.*, vol. 1, No. 15, 1982, pp. 361-367.
Wilkinson, "Transfer of Triplet State Energy and the Chemistry of Excited States", *J. Phys. Chem.*, 66:2569 (1962).
Elliot et al., *J. Phy. Chem.*, vol. 82, No. 4, 1978, A CIDEP Study of the Photoreduction of Quinones in the Presence of Phenols and 2-Propanol.
Gandelman et al., *J. Chrom.* 242 (1982) pp. 22-31.
Brinkman et al., *J. Chrom.* 217 (1981) pp. 463-471.

*Primary Examiner*—Barry S. Richman
*Assistant Examiner*—C. M. Delahunty
*Attorney, Agent, or Firm*—Barbara A. Shimei

[57] ABSTRACT

A process for detecting the presence of trace amounts of non-fluorescent soluble compounds each having at least one labile hydrogen atom in a carrier solution by adding a non-fluorescent quinone which is reducible to a fluorescent hydroquinone, and irradiating the resulting solution in the absence of oxygen with light of sufficient energy to cause the quinone to be reduced to a hydroquinone. The invention further provides a novel photochemical reactor—recording fluorometer combination and carrier liquid—quinone solution for performing the analysis.

11 Claims, 4 Drawing Figures

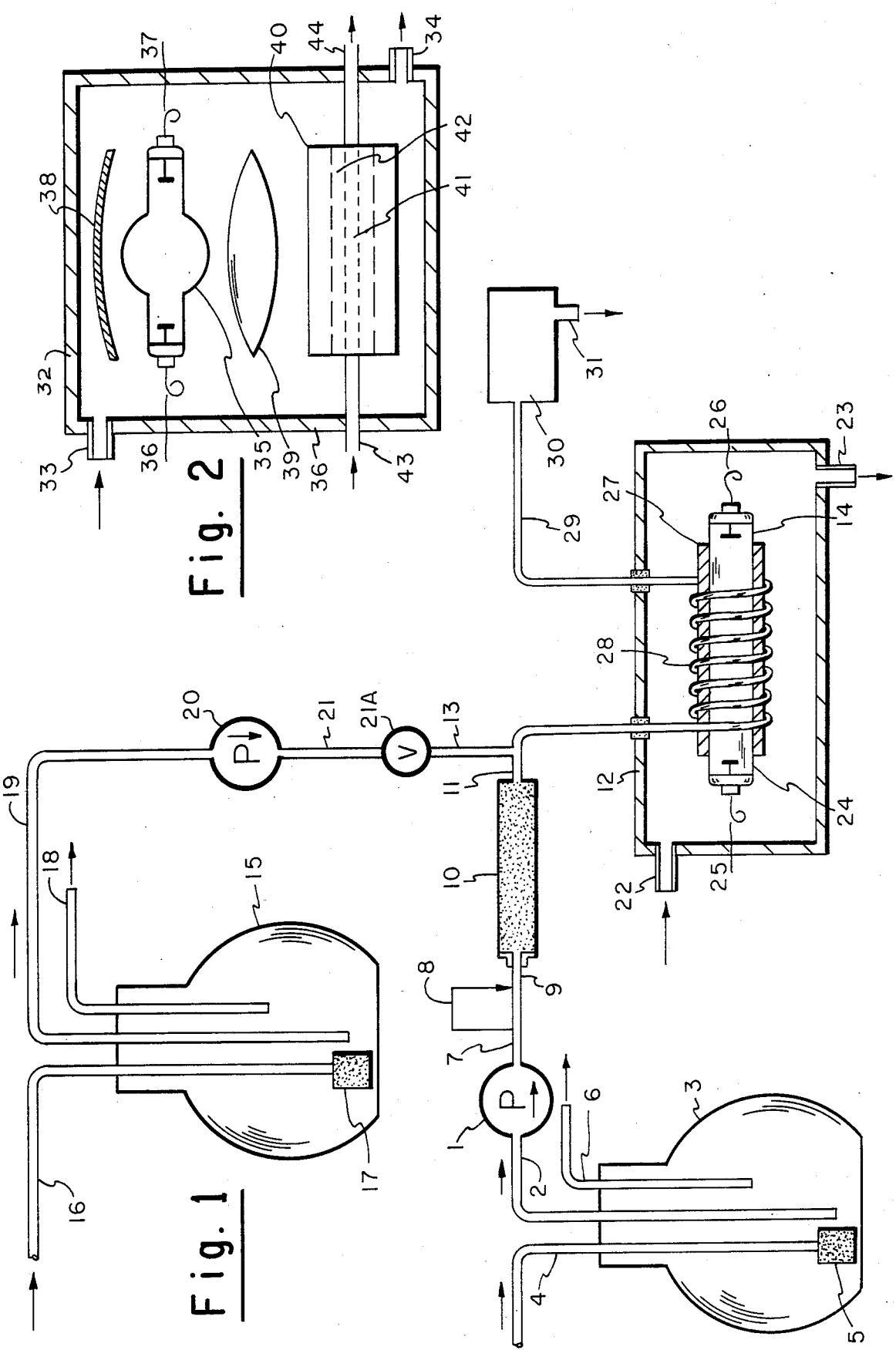

HIGH-PERFORMANCE LIQUID CHROMATOGRAPHY PROCESS AND APPARATUS AND COMPOSITION OF MATTER THEREFOR

The present invention relates to high-performance liquid chromatography. More particularly the invention relates to a novel method for the detection of certain non-fluorescing organic compounds particularly when present in trace amounts, to novel apparatus for the performance of the process, and to a novel carrier-quinone which is useful therein.

In recent years a demand has arisen, particularly in the life sciences, for methods for the detection of drugs, toxins, narcotics, poisons, hormones, vitamins and the like which are frequently present in trace amounts in blood, body excretions, drinking water, medicaments, beverages, cooked food, raw crops and soil. The method most often employed to detect these compounds (herein termed "analytes") is to pass a solution of the liquid of interest through a chromatographic column, which separates the analytes into segments or bands in the liquid, and then to irradiate the effluent from the column with ordinary or ultraviolet light. The amount of light absorbed or the intensity and wavelength of the fluorescence emitted by those analytes which fluoresce and the position of the respective analytes in the effluent from the column may permit the components of the analyte to be identified and quantified. However, most compounds do not fluoresce and many other compounds do not absorb either visible or ultraviolet radiation making these compounds difficult or impossible to detect by either absorption or fluorescence methods.

The present invention is based upon the discovery that most of the difficulties associated with the foregoing processes in instances where the analyte is non-fluorescent (as is usually the case) can be overcome by using the analyte as reducing agent in a photochemical reaction wherein a non-fluorescent quinone is reduced to a fluorescent hydroquinone with the aid of ultraviolet light. Comparison of the intensity of the fluorescence thus developed by each component of the analyte and the location of the components in the segments discharged from the column usually permits identification of the components of the analytes and often permits determination of the amounts of each component which is present. The process of the present invention thus provides a novel method for the quantitative and qualitative analysis of certain non-fluorescent organic compounds which are present in trace amounts, down to a few parts per million. When only one compound is present in the sample no chromatographic column is necessary.

The invention possesses the following advantages:

1. The process is simple and can be performed rapidly in apparatus composed of commercially available units. The longest step of the process (the photochemical reduction) has not required more than 60 seconds with low-intensity ultraviolet irradiation, and the time can be shortened to 10 seconds and even less by use of high-intensity ultraviolet irradiation. The materials which are preferably used in the process are commercially available. As a result, professional analysts can assemble the apparatus and make use of the process without having to learn any new technique or to procure special components.

2. The process does not require the analyte to absorb light or ultraviolet radiation, and this overcomes a limitation which is present in other chromatographic processes.

3. Only two chemicals are needed for performance of the process in most instances, and the entire apparatus can be made compact and portable. The apparatus thus can be transported to race tracks, arenas, stadiums, agricultural centers, hospitals, toxic material dump sites, etc. and used there to detect suspect compounds in the fluids there present. Also, gases and solids can be analyzed by dissolving the samples in a liquid.

4. The process is sensitive. It is capable of detecting most compounds within its scope in amounts as small as one part per million and in certain instances even less. It is capable of detecting in certain instances compounds which up to the present have been difficult or impossible to detect at such low concentrations.

5. In preferred embodiments the process is safe. It does not require high-intensity ultraviolet illumination, nor need it produce ozone at toxic level.

6. The process is at least two orders of magnitude more sensitive than the refractive index method which today is the most widely used method for the detection of trace amounts of compounds which do not absorb light or fluoresce, and it sharply excludes certain classes of compounds against which the refractive index method of analysis does not discriminate.

The present invention thus provides analysts with a most helpful tool.

Additional information and advantages are presented in the following papers by us:

"Liquid Chromatographic Detection of Cardiac Glycosides, Saccharides and Hydrocortisone Based on the Photoreduction of 2-tert-Butylanthraquinone" by M. S. Gandelman and J. W. Birks (in publication);

"Photoreduction-Fluorescence Detection of Aliphatic Alcohols, Aldehydes and Ethers in Liquid Chromatography", Anal. Chem. 54, 2131–2133 (1982).

See also Gandelman, Birks, Brinkman and Frei, "Liquid Chromatographic Detection of Cardiac Glycosides and Saccharides Based on the Photoreduction of Anthraquinone-2,6-Disulfonate" (in publication).

A photoprint of each of the foregoing papers is attached, respectively marked Exhibits A–C, and each is hereby incorporated by reference in the present specification.

The invention is capable of detecting trace amounts of the following compounds, which are of ecological, medical and industrial importance:

Acetaldehyde
Alcohols
Aldehydes
Allylic hydrocarbons
Amino acids
Attenolol
Benzylic hydrocarbons
Butanol
Captopril
Digitalis glycosides
Diethyl ether
Dioxane
Ethanol
Ethers
Ethylene glycol
Formaldehyde
Fructose
Glutaraldehyde Glycerol
1-Hexanol
Hydrocortisone
Isopropyl alcohol
Isobutyl alcohol
Isovaleraldehyde
Methanol
1-Propanol
2-Propanol
Propionaldehyde
Saccharides
Steroids
Sucrose
Valproic Acid The compounds which are most readily detected by the process of the present invention, so far as now known, are alcohols, aldehydes, amines, ethers, glycosides, and saccharides.

More in detail, the present invention provides a process for the detection of a substantially non-fluorescing organic compound having at least one labile hydrogen atom, that is, a compound containing at least one carbon-hydrogen bond having a dissociation energy less than 100 kcal./mol. in solution in a substantially non-fluorescing carrier liquid, which comprises: (1) dissolving in said solution a small amount as fluorogenic reagent for said compound a non-fluorescent quinone which is photochemically reducible to a fluorescent hydroquinone; (2) irradiating the resulting solution with ultraviolet light for a time sufficiently long to reduce at least a portion of said quinone to a hydroquinone by photochemical reaction with said non-fluorescent organic compound but not so long as to degrade said hydroquinone to a non-fluorescent derivative; and (3) irradiating the solution thus obtained under conditions insufficient to cause degradation of said hydroquinone to a nonfluorescent derivative, thereby causing the solution to fluoresce.

The invention further provides a process for the quantitative determination of a substantially non-fluorescing organic compound containing at least one carbon-hydrogen bond having a dissociation energy less than 100 kcal./mol. in solution in a substantially non-fluorescent carrier liquid, which comprises; (1) dissolving in said solution as fluorogenic reagent for said compound an effective amount therefore of a non-fluorescent quinone which is photochemically reducible to a fluorescent hydroquinone; (2) irradiating the resulting solution with light for a time sufficiently long to reduce at least a portion of said quinone to a hydroquinone by photochemical reaction with said non-fluorescent organic compound but not so long as to degrade said hydroquinone to a nonfluorescent derivative, said light having sufficient energy to cause reduction of said quinone to a fluorescent hydroquinone; (3) further irradiating the latter resulting solution under conditions insufficient to cause degradation of said hydroquinone to a nonfluorescent derivative thereby causing said solution to fluoresce; (4) recording the intensity of said fluorescence; and (5) comparing said record with a pre-prepared reference standard. Typically the standard is the record of the fluorescence of a set of laboratory standard solutions prepared in the same manner wherein each member of said set except the first was prepared from a starting solution which contained a larger amount of said non-fluorescing organic compound than the previous member of said set.

Apparatus suitable for carrying out the invention, that is, for detecting the presence of a trace amount of a substantially non-fluorescent organic compound containing at least one carbon-hydrogen bond having a dissociation energy less than 100 kcal./mol. in solution with a substantially non-fluorescent carrier liquid, comprises in combination and in series: (1) a photochemical reactor comprising an ultraviolet lamp, transparent tubing having an inlet end for admission of liquid to be exposed to radiation from said lamp, a middle portion position to receive ultraviolet radiation from said lamp, and a discharge end; (2) a recording fluorometer comprising a lamp, transparent fluorescence cell or cuvette having an inlet end, a middle portion positioned adjacent to said lamp and a discharge end, means for detecting fluorescence of liquid in said fluorescence cell while said liquid is being irradiated with light from said lamp, and means for recording the intensity of said radiation; and (3) a conduit connecting the discharge end of the tubing of said reactor with the inlet end of the tubing of said fluorometer.

The invention further provides a high-performance liquid chromatograph for the detection of a substantially non-fluorescing compound containing at least one carbon-hydrogen bond having a dissociation energy less than 100 kcal./mol. in solution in a substantially non-fluorescent carrier liquid having a dissolved content of a non-fluorescent quinone which is photochemically reducible to a fluorescent hydroquinone, which comprises in combination and in series: (1) a reservoir adapted to contain and to deoxygenate a quantity of carrier liquid; (2) a high-pressure pump adapted to force mobile carrier liquid through a packed chromatographic column; (3) a sample injector having a sample metering loop; (4) a chromatographic column; (5) a photochemical reactor comprising an ultraviolet lamp, transparent tubing having an inlet end for admission of liquid to be irradiated by said lamp, a middle portion positioned to receive light from said lamp and a discharge end; (6) recording fluorometer means comprising a lamp, transparent quartz cell or cuvette having an inlet end, a middle portion positioned adjacent to said lamp and a discharge end, means for detecting fluorescence of liquid in said cell or cuvette while said liquid is being irradiate with light from said lamp; and (7) conduits connecting said pump, sample injector, photochemical reactor and fluorometer together in series.

The invention further provides a composition of matter useful in the above-described high-performance liquid chromatographic process, which comprises: (1) as carrier component a major proportion of a mobile substantially non-fluorescent inert organic liquid and, dissolved therein, (2) a minor proportion as fluorogenic component of a substantially non-fluorescent quinone which is photochemically reducible to a fluorescent hydroquinone by reaction with a dissolved organic compound containing at least one carbon-hydrogen bond having a bond dissociation energy less than about 100 kcal./mol.

According to the invention the process is utilized in several modes.

The simplest mode occurs when it is desired merely to determine whether a sample to be analyzed contains a group of compounds capable of detection (or only one such compound). In such event there is no need to split the analytes into segments, and the analysis can be performed by adding a sufficient quantity of a fluorogenic reagent (a nonfluorescent quinone) to the sample, deoxygenating the sample with or without addition of diluent as may seem desirable, subjecting the resulting solution to sufficient ultraviolet radiation to effect reduction of at least a part of the fluorogenic reagent, and subjecting the product of the irradiation to examination by fluorometer to determine if the sample fluoresces under ultraviolet or visible light. The development of fluorescence is evidence that the sample contained the suspected analytes.

In the process, any diluent or carrier liquid used should be free from reactive impurities, and the fluorogenic reagent should be free of non-quinone reactive material.

Moreover, the material undergoing analysis should be free of oxygen and any other reactive gas at least during the time that it is undergoing ultraviolet irradiation, and preferably from the time that the fluorogenic reagent is added thereto. This can be accomplished by the use of a nitrogen aeration or sparging of the make-up solution and passage of the solution in stainless steel tubing up to the reactor.

Further, it is highly desirable that the added fluorogenic material and the diluent or carrier liquid be free from reactive impurities.

The amount of fluorogenic reagent which is added to the sample in any instance depends upon a number of independent variables such as the molecular weights of the particular fluorogenic compound selected and of the analyte, and the amount of analyte in the sample, and so cannot be calculated in advance. A suitable amount in any instance, however, can be readily ascertained by making a series of trials, preferably starting with a very low amount. A suitable amount is that which produces easily detectable fluorescence, and the amount which produces maximum fluorescence in the fluorometer is generally preferred.

It is likewise not possible to state numerically the preferred duration of exposure of the sample to ultraviolet radiation because this likewise depends on several independent variables such as the transparency of the tubing in which the sample is circulated near the lamp, the wattage of the lamp, and wavelengths of light which the lamp emits. The optimum duration in any instance is that which produces a highly fluorescent discharge. A decrease in the intensity of the fluorescence developed in the discharge during the series of trials is evidence that the irradiation has lasted too long (or that the intensity of the emission of the lamp has been too high), and that at least a part of the hydroquinone which is formed during the irradiation has undergone a degradation.

The detection of fluorescence in the discharge from the reactor, and the relative intensity of the fluorescence is made by any conventional recording fluorometer which provides a running trace to be made of this intensity of the sample under ultraviolet and visible light. The development of a sharp and high peak in the tracing of the fluorometer is evidence that a sufficient amount of a suitable fluorogenic reagent and a suitable intensity of ultraviolet irradiation have been used.

To determine quantitatively the amount of a single known compound in a sample, a series of calibrating runs is made under identical conditions except that in each succeeding run the amount of the analyte is increased to a probable maximum (or decreased to a probable minimum), and a plot is made of the intensity of the fluorescence which is developed by each run in the fluorometer. Comparison of the height (or the area) of the peak appearing on the tracing produced by the fluorometer for the unknown sample with the height of the peak in the plot permits a determination to be made of the percent of the analyte which is present in the unknown sample.

More often, the process is used to determine whether a sample contains suspect components and if so the number of such components in the sample, the identities of the components and the respective amounts thereof.

To this end, the sample, if desired after dilution with carrier liquid, is pumped through an appropriately packed chromatographic column where the analytes are separated into bands or segments and the discharge from the column with an appropriate content of fluorogenic reagent as determined above is subjected to ultraviolet irradiation, also as is described above, and is then allowed to flow through a recording fluorometer. The number of peaks which appear in the tracing from the fluorometer indicate the number of identifiable components in the analyte, and the relative heights of the peaks provide an indication of the relative amounts of the components in the sample. Where the nature of these components is known, a more accurate determination of the percentage of each can be made by performing a series of calibrating runs as described above for each component, plotting the results, and comparing the peaks on the test tracing with the plots obtained from each set of calibrating runs.

Comparison of the tracing from the fluorometer with tracings made of previously known compositions may permit identification of the components in the sample when the location on the tracing of the peaks in the tracing of the sample correspond with the location of the peaks on the reference standard.

In general, the compounds which are capable of detection by the process of the present invention are those which are substantially non-fluorescing and which contain at least one carbon-hydrogen bond having a dissociation energy less than 100 kcal./mol. The first requirement ensures that the analyte will not be, and will not contain a component having a native fluorescence which will mask in the fluorometer the fluorescence developed by the reduced quinone. The second requirement ensures that the compound will have a labile hydrogen atom which will be available under ultraviolet irradiation for reduction of the quinone.

In the process, it is advantageous to dilute the sample to permit the components therein to be well spaced in the discharge from the chromatographic column. Suitable solvents, generally termed "carrier liquids" in general are any organic compound which, preferably, is non-absorbing of ultraviolet light and which does not have the capacity of acting as a hydrogen donor with respect to a quinone under irradiation with ultraviolet light, that is, one which does not contain a carbon-hydrogen bond having a dissociation energy less than about 100 kcal./mol. or, if the compound does have a carbon-hydrogen bond of less than 100 kcal./mol. strength, then the compound must have a very slow rate of reaction with the quinone in the presence of ultraviolet light. Suitable carrier liquids conforming to there requirements include:

Acetonitrile
Carbon tetrachloride
1-Chlorohexane
2-Chlorohexane
Cyclohexane
Decane N,N-Dimethylacetamide
2,3-Dimethylhexane
Heptane
Hexane
Isopentane
Methylene chloride
Nonane
Octane
Pentane
Tetradecane
Propionitrile
Water Mixtures of two or more of the foregoing compounds can be used as carrier liquids in instances where they are mutually soluble. Thus acetonitrile-methylene chloride and acetonitrile-water solutions are suitable. Of these, acetonitrile-water solutions in about 80:20 to 20:80 ratio by volume are preferred because these solutions work well in chromatographic columns which contain hydrophobic coated particles and because they readily dissolve a wide variety of analytes and quinones.

The foregoing carrier liquids and mixtures thereof are not more viscous than glycerol, and so are readily pumpable.

The fluorogenic component can be any quinone which is non-fluorescent under ultraviolet and normal light, which is soluble in at least one carrier liquid at room or elevated temperature, and which is reducible to a hydroquinone which is fluorescent under ultraviolet and/or normal light, the reduction being effected by the photochemical action of ultraviolet light in conjunction with a dissolved organic compound containing at least one carbon-hydrogen bond having a bond dissociation energy less than 100 kcal./mol.

Quinones which are suitable for use as fluorogenic components and which conform to the above-stated requirements include:
2-Amino-9,10-anthraquinone
9,10-Anthraquinone
9,10-Anthraquinone-2-carboxylic acid, sodium salt
9,10-Anthraquinone-2,6-disulfonic acid, disodium salt
9,10-Anthraquinone-2-sulfonic acid, sodium salt
Benzoquinone
2-tert-Butyl-9,10-anthraquinone
2-Benzoquinonesulfonic acid, sodium salt
2-Ethyl-9,10-anthraquinone
2-Methyl-9,10-anthraquinone
1,4-Naphthoquinone
Phylloquinone
Vitamin $K_1$
Vitamin $K_3$ (Menadione)

Of these 9,10-anthraquinone, 2-tert-butyl-9,10-anthraquinone, and 9,10-anthraquinone-2,6-disulfonic acid, disodium salt are preferred because the quinones can be safely added to the carrier liquid in the make-up reservoir thereby avoiding the necessity for the separate pump, injection meter with loop and associated valves and conduits which would be needed for post-column addition of this material and because their reduction products fluoresce with extreme brightness under radiation, thereby increasing the sensitivity of the process. Moreover, the compounds pass through chromotographic columns packed with hydrophobic coated particles without affecting the action of the columns and without being affected by the hydrophobic nature of the columns.

The amount of fluorogenic component in the reaction mixture during irradiation may be and usually is very small. Since the weight of the analyte in the composition is usually negligibly small, the amount of the fluorogenic component is usually based on the weight of the carrier liquid component. In practice it has not been found necessary to have more than 1% by weight of fluorogenic component present, which is therefore regarded as the practical maximum, although more may be present if desired, since usually a stoichiometric excess is harmless. At the other extreme the minimum effective amount has not been established, but very satisfactory results have been obtained with 0.01% by weight of the fluorogenic material in the carrier solution, and no reason is seen why as little as 0.001% and even 0.00001% by weight would not prove useful in certain instances. This latter amount is therefore regarded as the practical minimum, although an intermediate amount of 0.001% might prove more generally useful and therefore preferable.

It has been found convenient to prepare a quantity of the carrier liquid and the fluorogenic component as a stock solution. Accordingly the present invention provides such a composition of matter which is useful in high-performance liquid chromatography, comprising: (1) as carrier component a major proportion of a substantially non-fluorescent inert organic liquid and, dissolved therein, (2) a minor proportion of a substantially non-fluorescent quinone which is photochemically reducible to a fluorescent hydroquinone by reaction with a dissolved organic compound containing at least one carbon-hydrogen bond having a bond dissocation energy less than about 100 kcal./mol. Preferably the carrier component is water-soluble and consists essentially of an 80:20 to 20:80 by volume acetonitrile:water solution. The preferred quinones are those which have been named above.

The invention provides apparatus for detecting the presence of a substantially non-fluorescing organic compound containing at least one carbon-hydrogen bond having a dissociation energy less than 100 kcal.-/mol. containing in solution therewith a substantially non-fluorescent quinone which is photochemically reducible to a fluorescent hydroquinone in a substantially non-fluorescent carrier liquid, which comprises in combination and in series: (1) a photochemical reactor comprising an ultraviolet lamp, transparent tubing having an inlet end for admission of liquid to be exposed to radiation from said lamp, a middle portion positioned to receive ultraviolet radiation from said lamp, and a discharge end; (2) recording fluorometer means comprising a lamp, transparent quartz cuvette having an inlet end, a middle portion positioned adjacent to said lamp and a discharge end, means for detecting fluorescence of liquid in said cuvette while said liquid is being irradiated with light from said lamp, and means for recording the intensity of said radiation; and (3) a conduit connecting the discharge end of the tubing of said reactor with the inlet end of the tubing of said fluorometer.

Preferably, the middle part of said tubing is in tubular knitted form so that it can be slipped as a sleeve over the ultraviolet tube, or is in crochetted ribbon form so that it can be wrapped around the tube. The loops of the knitting or crochetting promote turbulent flow of liquid in the tubing and so cause less dispersion of the previously separated bands of the analyte from the chromatographic column. Alternatively the middle part of the tubing can be positioned within a transparent oblong having a smooth side; the apparatus contains a lens adapted to focus light from the ultraviolet lamp upon the smooth side. When said tubing is gas-permeable, the reactor comprises means for preventing access of oxygen thereto. The lamp in the reactor can be a high-intensity ultraviolet lamp, but preferably is a low-intensity lamp i.e., a lamp having an output of less than about 20 watts. The lamp in the fluorometer is preferably adapted to emit light having a wavelength between about 250 nm. and 400 nm. The transparent tubing may have any convenient diameter, but capillary tubing is preferred to again reduce dispersion of analyte bands.

The invention further provides a high-performance liquid chromatograph capable of making analyses as are described above, which comprises in combination and in series; (1) a reservoir adapted to contain and to deoxygenate a quantity of carrier liquid; (2) a high-pressure pump adapted to force carrier liquid through a packed chromatographic column; (3) a sample injector having a sample metering loop; (4) a chromatographic column; (5) a photochemical reactor comprising an ultraviolet lamp, transparent capillary tubing having an inlet end for admission of liquid to be irradiated by said lamp, a middle portion to receive radiation from said lamp, and a discharge end; (6) recording fluorometer means comprising a lamp, transparent quartz cuvette having an inlet end, a middle portion positioned to receive light from said lamp and a discharge end, means for detecting fluorescence in the middle of said cuvette, and means for recording the intensity of said radiation; and (7) conduits connecting said pump, sample injector, photochemical reactor and fluorometer together in series.

Preferably the reservoir contains a gas diffuser at the bottom thereof to permit liquid therein to be deoxygenated by passage of nitrogen gas therethrough, the ultraviolet lamp is a low intensity lamp, and the apparatus further comprises a reservoir adapted to contain a solution of a photoreducible quinone, a low pressure pump, a stop check valve, and conduits connecting the reservoir with the low-pressure pump, the pump with the valve, and the valve with the conduit which connects the chromatographic column with the photochemical reactor.

The invention is further described by reference to the drawings, wherein:

FIG. 1 shows schematically apparatus suitable for the performance of analyses according to the present invention, permitting both pre-column and post-column introduction of solutions of fluorogenic reagents into the analyte solutions and showing transparent reactor tubing wound around the ultraviolet lamp;

FIG. 2 shows an alternative disposition of the reactor tubing with respect to the ultraviolet lamp;

Figure 4:
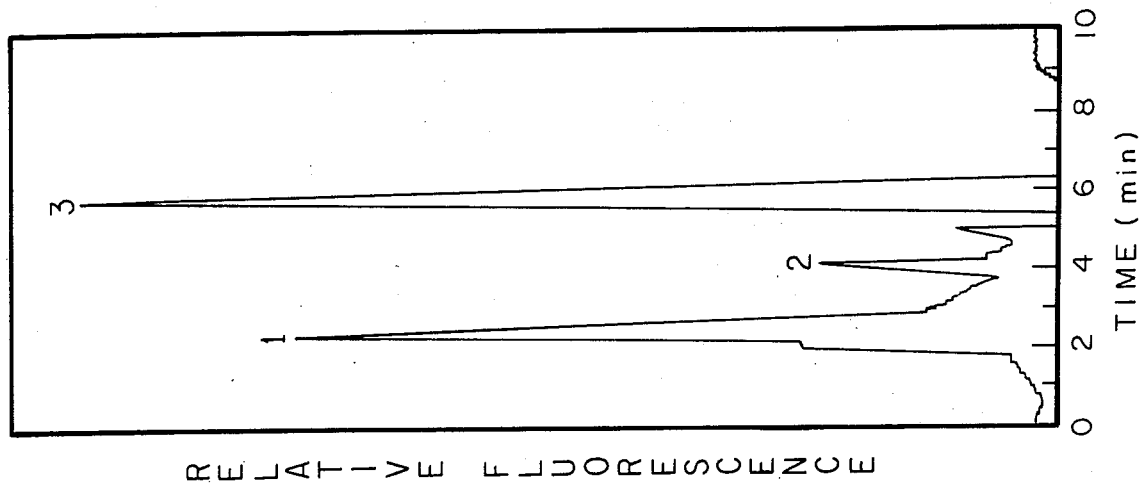
FIG. 4 reproduces a tracing produced by the fluorometer showing the relative intensities of fluorescence emitted by bands of analyte in the discharge from the reactor containing differing amounts of a reduced hydroquinone therein.

In FIG. 1, the apparatus is composed largely of commercially available units joined in combination and in series as shown. In the drawing, chromatographic high pressure pump 1 containing customary inlet and outlet check valves (not shown) suitable for forcing carrier fluid (either with or without a content of fluorogenic reagent as may be desired) at a pressure of 1,000 to 4,000 lb./in.$^2$ through a chromatographic packed column at a rate in the range of 0.1 to 10 ml. per minute supplied to pump 1 by opaque nonpermeable conduit 2 from opaque gas-impermeable make-up reservoir 3 containing deoxygenating gas admission conduit 4 ending in gas diffusion cap 5 at the bottom of reservoir 3. Reservoir 3 also contains vent 6 for discharge of spent deoxygenating gas. High-pressure opaque conduit 7 connects pump 1 with conventional sample injector-metering loop combination 8 which in turn is connected by conduit 9 to packed chromatographic column 10 provided with discharge conduit 11 leading to openable photochemical reactor jacket 12. Into conduit 11 is let optional conduit 13 containing stop check valve 21A permitting optional postcolumn introduction of fluorogenic solution from make-up reservoir 15 containing components 16, 17 and 18 which respectively duplicate previously—described components 4, 5 and 6. Conduit 19 permits solution to be drawn from reservoir 15 by low-pressure pump adapted to supply fluorogenic reactant solution at adequate pressure (usually 100–500 lb./in.$^2$) through conduit 21 to valve 21A. Jacket 12 contains orifices 22 and 23 permitting the introduction and discharge of inert gas or inert liquid (as may be desired) into the jacket to prevent access of oxygen or other reactive gas to the contents of the jacket. In jacket 12 removably mounted lamp 24 adapted to emit radiation of sufficient energy to cause quinones to be reduced to hydroquinones by compounds having a labile hydrogen atom as described, and as preferably an ultraviolet lamp is encased by removable Pyrex glass cylindrical sleeve 27 around which is coiled the middle portion of a length of transparent tubing 28 preferably capillary tubing made of poly(tetrafluoroethylene). The discharge end of tubing 28 is connected to conduit 29 which leads to conventional recording fluorometer 30 and is discharged therefrom to waste or storage through conduit 31.

In FIG. 2, optional openable jacket 32, provided with inlet and outlet orifices 33 and 34 for admission of inert gas or liquid to any gas-permeable reactor tubing within, contains removably mounted ultraviolet lamp 35 with electrical wires 36 and 37 and is backed by reflector 38 adapted to concentrate escaped light from lamp 35 with electrical wires 36 and 37 and is backed by reflector 38 adapted to concentrate escaped light from lamp 35 upon lens 39 which in turn is adapted to focus direct and reflected radiation from lamp 35 upon oblong transparent block or cuvette 40 having a smooth upper surface to decrease scattering of said radiation. Block 40 is traversed by longitudinal bore 42 in which the middle portion of capillary reactor tubing 41 is positioned. Jacket 32 becomes unnecessary when inlet and discharge ends of tubing 42 are formed of gas-impermeable material.

Figure 3:
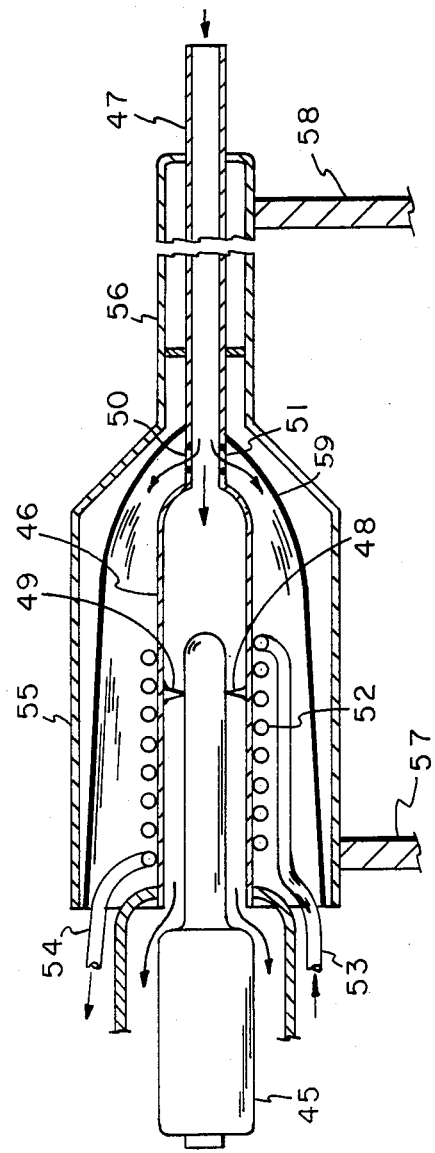
FIG. 3 shows schematically in section an alternative form of photochemical reactor.

In FIG. 3, high-intensity cylindrical ultraviolet lamp 45 is positioned axially within cylindrical quartz reactor tubing carrier 46 having one end 47 tapered to form inert gas/supply tube 47. Lamp 45 is centered axially within tubing carrier 46 by several alignment supports as needed, exemplified by supports 48 and 49. The discharge end of inert gas supply tube 47 contains vents or apertures 50 and 51 sufficiently large to permit part of the incoming stream of gas to flow over the interior of carrier tube 46 and thereby prevent access of oxygen to these portions of the apparatus. The mid portion of tubing carrier 46 is wound with a length of cylindrical transparent capillary reactor tubing, preferably poly(tetrafluoroethylene); the inlet and discharge ends 53 and 54 of said tubing project from the discharge end of said tubing carrier. Tubing carrier 46 wound with said reactor tubing fits loosely within cylindrical Pyrex glass jacket 55 having cylindrical tapered end 56 which closes with a gas-tight fit around inert gas supply tube 47 providing support for said tube. The discharge end of tubing carrier 46 is supported by tapered stainless steel tube 57 and the discharge end of jacket 55 is supported by bracket 58. Tapered or wrap cylinder 59 of metal foil attending beyond vents 50 and 51 reflects escaped radiation to said reactor tubing.

The above-described reactor is adapted to replace the reactor of FIG. 1, and is employed in the same manner as that reactor.

FIG. 4 is a reproduction of the tracing obtained by passage through a recording fluorometer of a deoxygenated hydroquinone-solvent-2-tert-butyl-9,10 -anthraquinone solution containing 20 ng. of hydrocortisone which had been irradiated with ultraviolet light in a reactor corresponding to that of FIG. 3 under a high-intensity ultraviolet lamp. From previous analyses it is known that peaks 1 and 3 represent respectively the solvent and impurity in the solvent, and that peak 2 represents the hydrocortisone. The tracing clearly shows that the process is capable of detecting this minute amount of hydrocortisone.

The invention is further illustrated by the examples which follow. The examples are preferred embodiments of the invention, and are not to be construed in limitation thereof.

EXAMPLE 1

The following illustrates the detection of a lower alcohol by the process of the present invention, performed essentially by hand without use of pump, metering loop or chromatographic column.

Into a make-up reservoir according to FIG. 1 is charged 250 cc. of an 80:20 by volume acetonitrile:water solution and into this is pipetted 0.25 ml. of a 1% by weight solution of C.P. ethanol in distilled water as analyte, followed by sufficient amount of a aqueous solution of 1,4-naphthoquionone to provide a $4.0 \times 10^{-4}$ molar solution of the quinone as fluorogenic reactant. The solution is deoxygenated by bubbling nitrogen gas therethrough for 20 minutes, after which a sample is withdrawn by a quartz capillary tube which is subjected to ultraviolet radiation for 30 seconds after which the capillary is placed in a fluorometer for determination of the fluorescence of its contents. A positive reading which represents an increase in fluorescence over an identically prepared sample which does not contain any C.P. ethanol is provided by the fluorometer, showing that the process is capable of detecting trace amounts of ethanol.

EXAMPLE 2

The following illustrates the analysis of a soft drink containing trace amounts of common food saccharides by the method of the present invention.

The apparatus used corresponds with that of FIG. 1, the chromatographic column being of the amino type, that is, packed with 5-$\mu$m silica particles having aminoalkyl chains bonded thereto so as to render the particles hydrophilic.

Into the make-up reservoir is charged 250 cc. of an 80:20 by volume solution of acetonitrile and water and also 0.0067% by weight of 2-tert-butyl-9,10-anthraquinone, which is deoxygenated by bubbling nitrogen gas therethrough for 20 minutes. The carrier liquid pump is then started and allowed to run flushing out the system at the rate of 1.0 ml. of solution per minute. Nitrogen gas is flowed into the photochemical reactor jacket flushing out all the oxygen therein. The metering loop of the sample injector having a capacity of 20 $\mu$l. is filled with the solution to be analyzed. The tracing or graph provided by the fluorometer shows four strong sharp peaks which from prior work are known to evidence the presence in the sample of fructose, glucose, and sucrose, together with the solvent.

EXAMPLE 3

The following illustrates the analysis of a solution containing a dissolved digoxin tablet by the method of the present invention.

The apparatus of FIG. 1 is used except that the photochemical reactor is replaced by the alternate reactor of FIG. 3. The equipment for post-column introduction of the quinone reagent is not used.

The starting-up procedure of Example 2 is repeated, except that the carrier solution is a 60:40 by volume acetonitrile:water solution. To this is added sufficient of an acetonitrile solution of 2-tert-butyl-9,10-anthraquionone to provide a $5.1 \times 10^{-4}$ molar concentration of anthraquinone in the carrier liquid. The resulting solution is pumped to the column at the rate of 1.0 ml. per minute. A solution of a digoxin tablet is added to the carrier solution by means of the measuring loop. The residence time of the solution under the ultraviolet lamp is 21 seconds. The tracing provided by the fluorometer shows very strong peaks which from prior work are known to represent lactose, 200 ng. of digoxin, the solvent and a solvent impurity.

EXAMPLE 4

The following illustrates the analysis of a sample composed of a standard hydrocortisone (a steroid hormone) in an impure organic solvent.

The chromatographic system used is composed of a high-pressure chromatographic pump (Altex 100A), a sample injector with a 20-$\mu$l. loop (Rheodyne 7120), a chromotographic column (Altex, 250 mm.$\times$4.6 mm.) packed with a 10-$\mu$m. silica particles having hydrophobic $C_{18}$ chains bonded thereto, a photochemical reactor, and a fluorometer.

The pump, the sample injector and the chromatographic column are connected together by high-pressure stainless steel tubing.

The photochemical reactor corresponds with that shown in FIG. 3, and is fabricated by inserting a 13-mm. outside diameter quartz tube through a supporting union (Cajon Ultra-Torr) carrying a Cajon Ultra-Torr adaptor of appropriate dimensions at each end. Two slots are cut in the quartz tube as vents to permit nitrogen gas to escape from the tube and so maintain a nitrogen atmosphere around the reactor tubing. The quartz tube is flared to an outside diameter of 19 mm. on emergence from the Ultra-Torr union. Around the flared portion of the quartz tube is coiled 80 cm. of polytetrafluoroethylene capillary tubing having an outside diameter of 1.5 mm. and an inside diameter of 0.50 mm. A sheet of aluminum foil is wrapped around the coil to reflect the photons which pass therethrough. Three quartz alignment supports are placed on the inner surface of the flared portion of the quartz tubing. An ultraviolet lamp (Pen-ray lamp of Ultra-Violet Products Inc., San Gabriel, CA) is slid along the flared tube to a position within the portion which carries the coil, as shown in FIG. 3. The lamp is centered in the tube by the alignment supports. Finally a Pyrex glass tube (32 mm. in outside diameter with one end reduced to 19 mm. in outside diameter in order to fit inside the Cajon union) is slid over the 19-mm. outside diameter quartz tube and its narrow end is housed in the union. When the apparatus is in operation this tube is continually swept with nitrogen and prevents access of oxygen to the coils.

The entire apparatus is supported by two steel clamps, one around the ultraviolet lamp assembly and the other around the Cajon fitting.

The detection component is a recording fluorometer (Schoeffel FS-970) with the excitation wavelength set at 375 nm. and with a 470-nm. filter on the emission side.

The photochemical reactor is placed between the chromatographic column and the fluorometer.

Into a make-up reservoir is charged 250 cc. of a stock solution of 60:40 by volume acetonitrile:water solution containing a $2.5 \times 10^{-4}$ molar concentration of 2-tert-butyl-9,10-anthraquinone. The resulting solution in this reservoir is deoxygenated by bubbling nitrogen gas therethrough, and the high pressure pump is started thereby flushing out the system with the carrier solution at a flow rate of 1 ml. per minute, thus providing a residence time of the solution in the photochemical reactor of 21 seconds.

The lamps in the reactor and in the fluorometer are switched on, and nitrogen gas at room temperature is admitted into the reactor at a sufficiently rapid rate of flow to sweep all oxygen from the interior of the apparatus and to prevent the polymer tubing from melting.

The sample injector loop is then charged with 20 µl. of an aqueous solution containing 0.1 p.p.m. by weight of a synthetic standard hydrocortisone in a commercial organic solvent, and the charge is admitted into the stream of carrier solution.

The chart from the fluorometer shows the strong peak at 4.2 minutes which is characteristic in this procedure of hydrocortisone, plus very strong peaks at 2.3 and 5.8 minutes which are respectively characteristic of the solvent and of an impurity in the solvent.

EXAMPLE 5

The procedure of Example 4 is repeated in the same apparatus as is used therein, except that an extracted hydrocortisone cream (a pharmaceutical product) is the sample.

A tracing with peaks similar to that obtained in Example 4 is obtained, except that the 4.2 minute peak (the hydrocortisone peak) is very strong and the 2.3 and the 5.8 minute peaks are very weak, thereby showing that the concentration of hydrocortisone in the sample is very high and that the concentrations of the solvent and of the solvent impurity are each very low.

We claim:

1. Process for detecting a substantially non-fluorescing organic compound containing at least one carbon-hydrogen bond having a dissociation energy less than 100 kcal./mol. in solution in a substantially non-fluorescent carrier liquid, which comprises: (1) dissolving in said carrier liquid containing said organic compound an effective amount, as fluorogenic reactant for said compound, of a non-fluorescent quionone which is photochemically reducible to a fluorescent hydroquinone by reaction with said organic compound under ultraviolet light; (2) irradiating the resulting solution with ultraviolet light for a time sufficiently long and with sufficient energy to reduce at least a portion of said quinone to a hydroquinone by photochemical reaction with said non-fluorescent organic compound but not so long as to degrade said hydroquinone to a non-fluorescent derivative; and (3) further irradiating said reduced solution with one of ultraviolet or visible light under conditions insufficient to cause degradation of said hydroquinone to a nonfluorescent derivative thereby causing the solution to fluoresce whereby said organic compound is detected.

2. Process according to claim 1 wherein said non-flourescing organic compound is ethanol.

3. Process according to claim 1 wherein said carrier liquid is an 80:20 to 20:80 by volume acetonitrile:water solution.

4. Process according to claim 1 wherein said quionone is 9,10-anthraquinone.

5. Process according to claim 1 wherein said quionone is 2-tert-butyl-9,10-anthraquinone.

6. Process according to claim 1 wherein the quinone is the disodium salt of 9,10-anthraquinone-2,6-disulfonic acid.

7. Process according to claim 1 wherein the quinone is 1,4-naphthoquinone.

8. Process according to claim 1 wherein the quinone is non-ionic, and further comprising the step of subjecting the carrier liquid containing said quinone and said organic compound to chromatography after step (1) and before step (2).

9. Process according to claim 1 comprising the additional step of subjecting said organic compound in solution in said carrier liquid to chromatography before step (1).

10. Process for the quantitative determination of a substantially non-fluorescing organic compound containing at least one carbon-hydrogen bond having a dissociation energy less than 100 kcal./mol. in solution in a substantially non-fluorescent carrier liquid, which comprises: (1) dissolving in said carrier liquid containing said organic compound an effective amount, as fluorogenic reactant for said compound, of a non-fluorescent quinone which is photochemically reducible to a fluorescent hydroquinone by reaction with said compound under ultraviolet light, (2) irradiating the resulting solution with ultraviolet light for a time sufficiently long to reduce at least a portion of said quionone to a hydroquinone by photochemical reaction with said non-fluorescent organic compound but not so long as to degrade said hydroquinone to a non-fluorescent derivative; (3) irradiating said reduced solution with one of ultraviolet or visible light under conditions insufficient to cause degradation of said hydroquinone to a nonfluorescent derivative thereby causing the solution to fluoresce; (4) recording the intensity of said fluorescence; and (5) comparing said record with a reference standard.

11. Process according to claim 10 wherein said carrier liquid contains more than one substantially non-fluorescing organic compound containing at least one carbon-hydrogen bond having a dissociation energy less than 100 kcal./mol.

* * * * *

UNITED STATES PATENT AND TRADEMARK OFFICE
CERTIFICATE OF CORRECTION

PATENT NO. : 4,656,141
DATED : 7 April 1987
INVENTOR(S) : John W. Birks and Mitchell S. Gandelman It is certified that error appears in the above-identified patent and that said Letters Patent is hereby corrected as shown below:

In column 1, after the title and before line 7, please insert the following paragraph:

--The invention described herein was made in the course of work partly supported by a grant from the National Science Foundation.--

Signed and Sealed this

Twenty-third Day of August, 1988

Attest:

DONALD J. QUIGG

*Attesting Officer*  *Commissioner of Patents and Trademarks*